US00PP23724P2

(12) United States Plant Patent
McCollum et al.

(10) Patent No.: US PP23,724 P2
(45) Date of Patent: Jul. 9, 2013

(54) MANDARIN TREE NAMED 'US EARLY PRIDE'

(50) Latin Name: *Citrus reticulata*
Varietal Denomination: US Early Pride

(75) Inventors: Thomas G. McCollum, Vero Beach, FL (US); Jack Hearn, Valdosta, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/931,765

(22) Filed: Feb. 10, 2011

Related U.S. Application Data

(60) Provisional application No. 61/402,096, filed on Aug. 24, 2010.

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

U.S. PATENT DOCUMENTS

| | | | |
|---|---|---|---|
| PP2,714 | P | 2/1967 | Darrow et al. |
| PP8,219 | P | 5/1993 | Vardi et al. |
| PP10,480 | P | 7/1998 | Nadori |
| PP13,460 | P2 | 1/2003 | Vardi et al. |
| PP13,616 | P2 | 3/2003 | Vardi et al: |
| PP13,617 | P2 | 3/2003 | Vardi et al. |
| PP13,624 | P2 | 3/2003 | Vardi et al. |
| PP13,634 | P2 | 3/2003 | Vardi et al. |
| PP13,709 | P2 | 4/2003 | Vardi et al. |
| PP15,461 | P3 | 1/2005 | Roose et al. |
| PP15,703 | P3 | 3/2005 | Roose et al. |
| PP16,289 | P3 | 2/2006 | Roose et al. |
| PP18,520 | P3 | 2/2008 | Recupero et al. |
| PP18,568 | P3 | 3/2008 | Recupero et al. |
| PP20,688 | P3 | 1/2010 | Janse van Rensburg |
| 2010/0017926 | P1 | 1/2010 | Lucas et al. |
| 2010/0017927 | P1 | 1/2010 | Lucas et al. |
| 2010/0125922 | P1 | 5/2010 | Gmitter, Jr. et al. |

OTHER PUBLICATIONS

Froneman et al. Promising seedless citrus selections from the ITSC mutation breeding programme. Subtropica vol. 17 No. 12 Dec. 1996.*

Hearn The Fallglo citrus hybrid in Florida. Proc. Fla. State Hort. Soc. 100:119-121. 1987.*

Growing Produce, What's New in Citrus?, 2009, http://www.growingproduce.com/varieties/citrus/varietynews/?storyid=1537.

Peter Chaires, New.Varieties Development & Management Corp., New Variety Update, http://stlucie.ifas.ufl.edu/pdfs/citrus/2010%20Fl%20Citrus%20Show%20Presentations/Chaires%20Indian%20River%20Citrus%20Show%202010_NVDMC_Chaires.pdf.

NVDMC Update, 2008, http://postharvest.ifas.ufl.edu/Events/Packinghouse%20Day%202008/Chairs/%20-%202008%20NVDMC%20Update.pdf.

* cited by examiner

*Primary Examiner* — Annette Para
(74) *Attorney, Agent, or Firm* — Gail E. Poulos; Lesley Shaw; John D. Fado

(57) ABSTRACT

A new and distinct mandarin cultivar which originated from seed produced by a hand pollinated cross of OSC 1466 (non-patented)×ORUS 1117-11 (non-patented) is provided. It is distinguished by production of fruit that combines early season maturity, large fruit size, smooth rind texture with deep orange color, and a rich sweet flavor. It further distinguishes itself by being very low seeded and relatively easy to peel.

4 Drawing Sheets

Latin name of the genus and species: The mandarin cultivar of this invention is botanically identified as *Citrus reticulate.*

Variety denomination: The variety denomination is 'US Early Pride'.

BACKGROUND OF THE INVENTION

The present invention is to a new and distinct variety of mandarin orange tree which is named 'US Early Pride'. 'US Early Pride' is a mandarin selection developed by the United States Department of Agriculture Agricultural Research Service at Groveland, Fla. from an irradiated bud of the diploid mandarin cultivar 'Fallglo', an early season maturing variety. The pedigree of 'Fallglo' is 'Bower' by 'Temple'.

'US Early Pride' originated as a single plant and was asexually reproduced by grafting budwood onto rootstocks. 'US Early Pride' was selected and propagated as follows. Irradiation of budwood from 'Fallglo' trees was accomplished in 1991 using 3 k RAD units of gamma irradiation from a Cobalt-60 irradiation source. Buds from this irradiation were propagated onto rootstocks in the greenhouse at the A.H. Whitmore Citrus Research Foundation Farm in Lake Co., Fla. where the trees were grown to field-plantable sized trees. These trees were planted in 1992 at the A.H. Whitmore farm. Fruit on the trees were evaluated in 1995 and two trees producing seedless fruit were identified. One of the trees (evaluated as 1-62-122, 'US Early pride') preformed better than the other and was selected for further evaluation. Buds were taken in 1996 and trees were propagated onto four rootstocks: Swingle, Cleopatra mandarin, sour orange and sun chu sha. Twenty trees were planted at the A.H. WHITMORE farm in 1997. Fruit production on these trees commenced in 2000. Additional propagations of 'US EARLY PRIDE' were maintained in the greenhouse at the A.H. WHITMORE farm.

BRIEF SUMMARY OF THE INVENTION

All major color code designations are made with reference to The Royal Horticultural Society Color Chart designations.

The present invention provides a novel mandarin variety having the characteristics described and illustrated herein. The variety, 'US EARLY PRIDE', is a mandarin selection developed at the USDA in Lake Co., Fla. from an irradiated bud of the diploid mandarin cultivar 'Fallglo', an early season maturing variety. 'US EARLY PRIDE' combines early season maturity, moderately sized fruit, pebbled rind texture with a deep orange color, and a rich sweet flavor similar to 'Fallglo'. It further distinguishes itself by being very low seeded (<1 seed/fruit) and relatively easy to peel.

Early maturing mandarin cultivars in production include 'Fallglo' (the original cultivar from which 'US EARLY PRIDE' was derived). 'Fallglo' is seedy (approximately 20-40 seeds/fruit). We are not aware of other early season mandarins that are low seeded.

BRIEF DESCRIPTIONS OF THE DRAWINGS

DETAILED DESCRIPTION OF THE INVENTION

Figure 1:
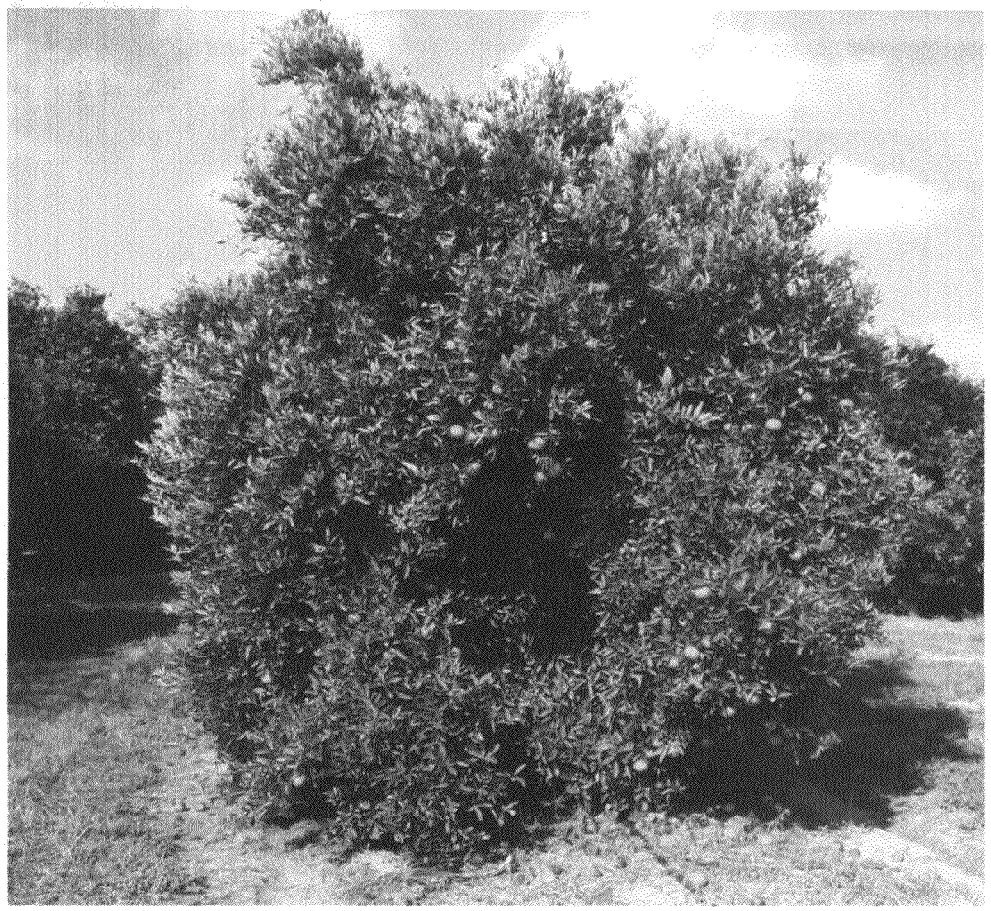
FIG. 1 illustrates a 14-year-old tree of 'US EARLY PRIDE' on Swingle rootstock.
Figure 2:
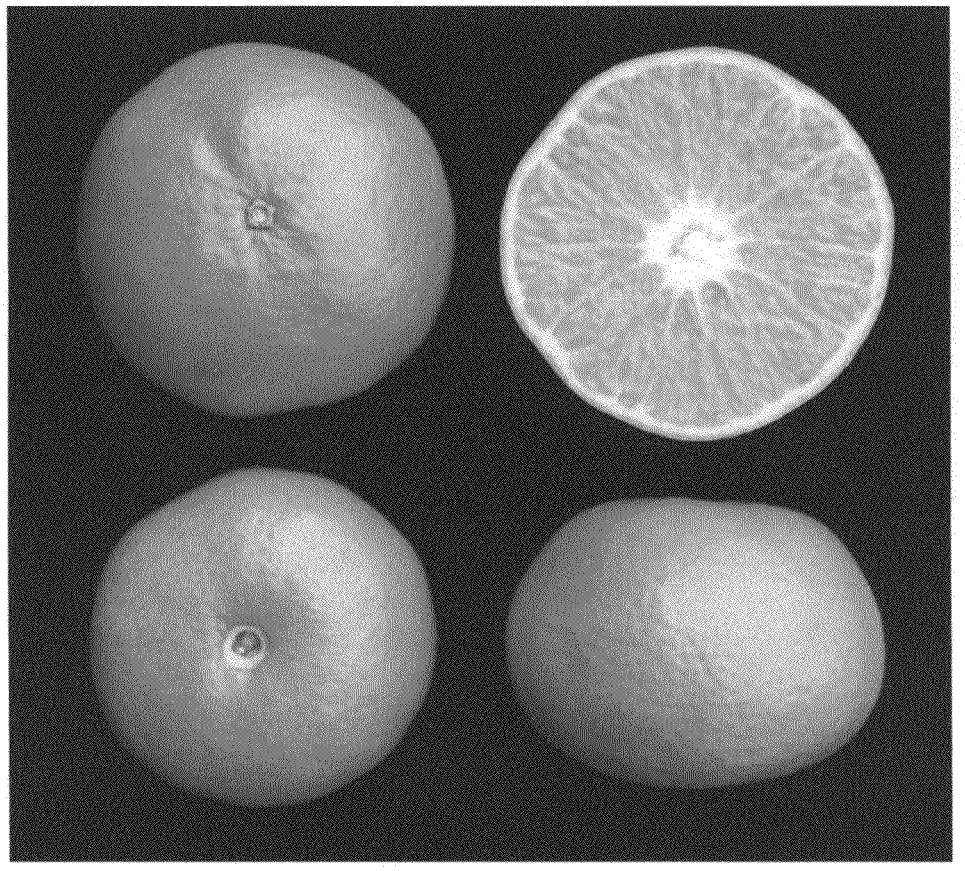
FIG. 2 illustrates fruit of 'US Early Pride' sampled from a 14-year-old tree at Lake Co., Fla. in 2008.
Figure 3:
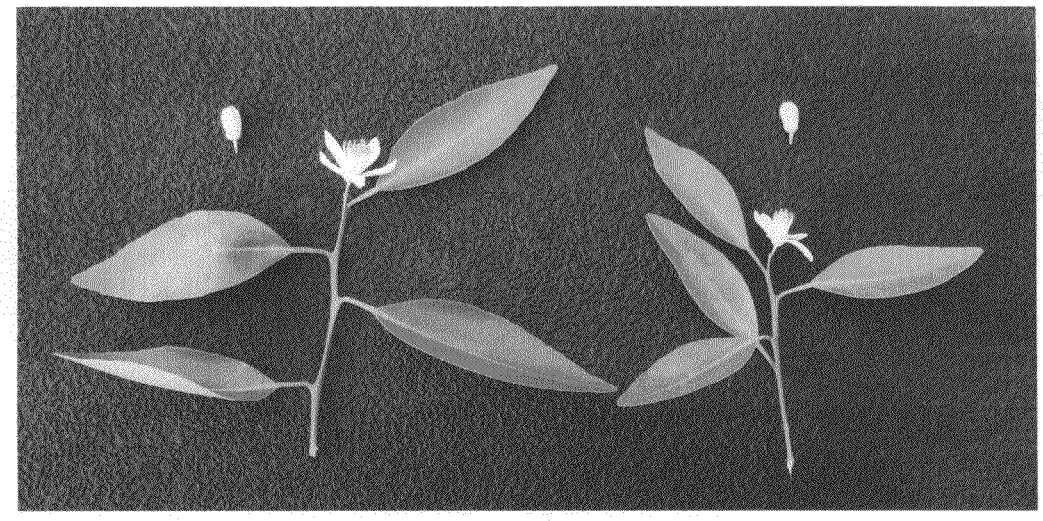
FIG. 3 illustrates clusters of 'US Early Pride' fruit on a 14-year-old tree at Lake Co., Fla. in 2008.
Figure 4:
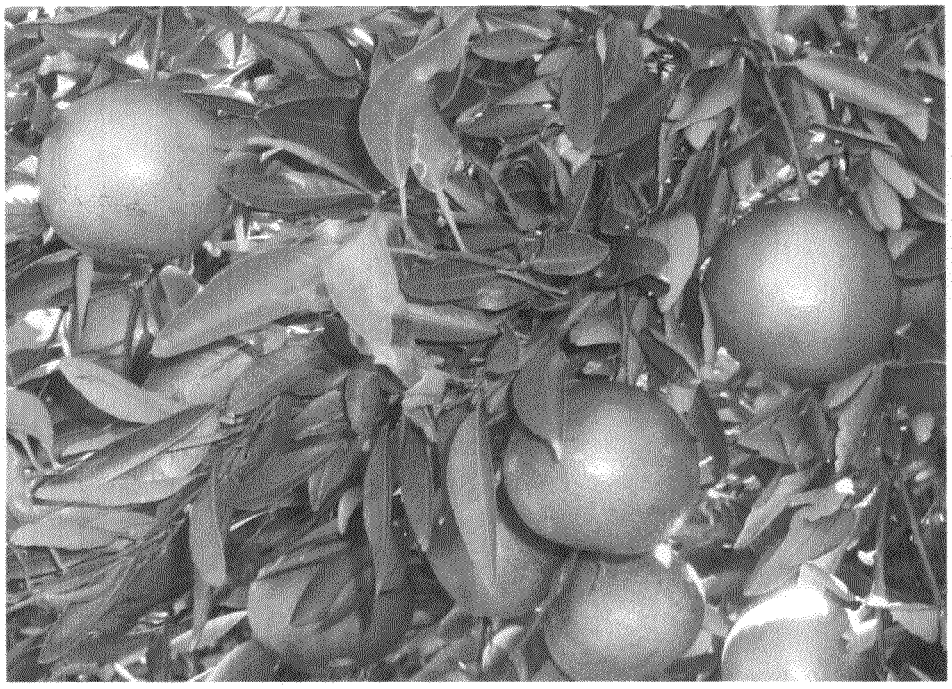
FIG. 4 illustrates a floral inflorescence of 'US Early Pride'.

Evaluation of 'US Early Pride' began on the original tree at A.H. WHITMORE farm in 1995. Tree size, growth and fruit production characteristics and fruit quality characteristics have been compared to 'Fallglo' from the same location. 'US Early Pride' trees have also been evaluated for two years at the USDA farm in St. Lucie Co., Fla.

Tree size and growth characteristics of 'US Early Pride' have been consistent with 'Fallglo' throughout the evaluation. Growth of both 'Fallglo' and the 'US Early Pride' selection has generally been upright in the first five years followed by a tendency to grow into spherical shape in ensuing years. The 14 year-old 'US Early Pride' tree at the A.H. Whitmore farm averaged approximately 3.7 m tall and approximately 4.1 m wide with normal upright growth habit yielding a canopy volume of approximately 32.7 $m^3$. In comparison 14 year-old 'Fallglo' tree have averaged 3.4 m tall and 3.0 m wide.

Scion circumference for 'US Early Pride' on rootstock was approximately 55 cm with the rootstock circumference approximately 76 cm. Scion circumference for 14 year-old 'Fallglo' trees averaged 51 cm.

'US Early Pride' distinguishes itself by being very low seeded (<1 seed per fruit) in all situations of cross-pollination, differing from 'Fallglo' which will set as many as about 40 seeds in cross-pollinated situations. In Lake Co., Fla. 'US Early Pride' fruit matures in the fall (October). 'US Early Pride' holds its fruit quality characteristics through November. Fruit size is large, approximately 58 mm in height× approximately 68 mm width) averaging approximately 145 grams per fruit. Fruit are oblate in shape with a deep orange rind color, RHS 22A and a smooth rind texture. Flesh color is deep orange (RHS N25B) and finely textured. Fruit are juicy, with a rich sweet flavor when mature. The fruit are relatively easy to peel. Tree growth habit is upright with production commencing in the second year after planting. Alternate bearing does not appear to be a problem. 'US Early Pride' was known throughout experimental evaluations as 1-62-122. The Royal Horticultural Society (R.H.S.) color numbering system is used herein for the color description of the rind, seed bark, leaf, flower, flesh color and other interest of the 'US Early Pride' tree.

Leaves of 'US Early Pride' are ovate in shape and convex in cross section, with an acuminate apex with slight serration and a cuneate base and are dark green in color, leaf abaxial color is RHS 137C (Green) and Leaf adaxial color is RHS 137 B (Green) (Table 2). Petioles are short and normal lacking wings. The selection is thornless. Flowers of 'US Early Pride' are hermaphroditic with white petals and yellow anthers and are borne in clusters. In Lake Co. Fla. buds form in late-January. Flowering occurs late February through early-April. Flowers have a medium fragrance. Pollen viability for 'US Early Pride' is very low (<10% germination). Pollen grains are smaller (18-20 microns) in comparison to 'Fallglo' (ca. 90% germination, pollen grains ca. 50 microns in diameter).

Fruit of 'US Early Pride' are oblate with no neck (Table 1). The fruit has the tendency to produce a navel at the blossom end. The fruit is large for a mandarin averaging 68 mm in diameter and 58 mm in height with a smooth, strong orangeish yellow rind color (RHS 22A) and relatively conspicuous, slightly raised oil glands (Table 4). The rind in somewhat adherent (relatively easy to peel) at maturity and relatively thin averaging approximately 2.7 mm in thickness. The fruit interior has a fine flesh texture with 11-13 segments and a hollow axis of medium size at maturity. The fruit are juicy averaging slightly over 55% juice and average 145 g in weight. The soluble solids, acids and solids/acid ratio for 'US Early Pride' is shown in Table 3.

TABLE 1

Fruit characteristics of 'US Early Pride' mandarins.

| | |
|---|---|
| Fruit shape | oblate |
| Fruit diameter | 68 mm |
| Fruit height | 58 mm |
| Fruit: shape of basal end | flat |
| Fruit: shape of distal end | flat |
| Fruit neck | Not present |
| Style | Not persistent |
| Rind texture | Smooth |
| Oil glands | Conspicuous, slightly raised |
| Rind color | RHS 22A (Orange) |
| Rind thickness | 2.7 mm |
| Albedo thickness | 1.2 mm |
| Albedo color | RHS 158A (Yellow white) |
| Rind adherence | moderately weak |
| Rind separation | relatively easy |
| Flesh (pulp) color | RHS N25B (Orange) |
| Flesh (pulp) texture | fine |
| Number of segments | 11-13 |
| Axis: structure | hollow |
| Axis: size | 8.3 mm |
| Navel presence | occasional |
| # seeds/fruit | <1 on average (cross pollinated conditions) |
| Seed embryonic | monoembryonic |
| Seed coat color | RHS 157A (Yellow white) |
| Seed cotyledon color | RHS 145C (Yellow green) |
| Seed inner coat color | RHS 166D (Greyed orange) |
| Fruit weight | 145 g |
| % Juice | 55% |
| % Soluble solids (at maturity) | 11-12% |
| % Acid (at maturity) | 1.1-0.9% |
| Season of maturity | early (mid October-late November) |
| Fruit holding ability on tree past maturity | 1 month |
| Fruit quality after storage (x temp., Y days) | Excellent (5° C., 21 days) |

TABLE 2

Tree, leaf, and seed characteristics (for X year old trees). Data from Lake Co., FL.

| | |
|---|---|
| Tree height | 3.7 m |
| Crown diameter | 4.1 m |
| Crown shape | upright |
| Trunk circumference (for scion on XX rootstock) | 55 cm |
| Trunk surface texture | Smooth |
| Bud-union characteristics | shelf with Swingle citrumelo |
| Rootstock-scion compatibility | No incompatibility known |
| Tree vigor | moderately vigorous |
| Bark color | RHS N 199A |
| Leaf shape | ovate |
| Leaf cross section | concacave |
| Leaf blade length | 6.8 cm |
| Leaf blade width | 2.8 cm |
| Leaf apex | acuminate |
| Leaf base | cuneate |
| Leaf abaxial color | RHS 137C (Green) |
| Leaf adaxial color | RHS 137B (Green) |
| Petiole length | 12 mm |
| Petiole width | 1.2 mm |
| Petiole color | RHS 37C (Green) |
| Thorniness | Not present |
| Inflorescence type | Clustered |
| Flowering habit | Flowers once per year |
| Flower size | 9 mm (Small) |
| Flower structure | complete |
| Petal color | white |
| Anther color | yellow |
| Pollen size | ca. 20 microns |
| Pollen viability | low (<10% germination) |

TABLE 3

Mean and standard deviation (s.d.) of soluble solids, acid and solids/acid ratio for 'US Early Pride' and 'Fallglo' (control trees) 2009 crop year.

| | 'Fallglo' | | US Early Pride' | |
|---|---|---|---|---|
| | Mean | sd | Mean | sd |
| | Total soluble solids | | | |
| 2-October | 10.6 | 0.29 | 9.65 | 0.25 |
| 14-October | 10.3 | 0.3 | 10.3 | 0.1 |
| 29-October | 11.3 | 0.1 | 10.7 | 0.17 |
| 13-November | 11.7 | 0.17 | 11.3 | 0.17 |
| 25-November | 12.3 | 0.4 | 11.9 | 0.17 |
| | Total acidity | | | |
| 2-October | 1.2 | 0.08 | 2.5 | 2.4 |
| 14-October | 1.2 | 0.08 | 1.1 | 0.1 |
| 29-October | 1.1 | 0.09 | 1.0 | 0.1 |
| 13-November | 1.0 | 0.08 | 1.0 | 0.1 |
| 25-November | 0.9 | 0.12 | 0.9 | 0.1 |
| | Solids/Acid ratio | | | |
| 2-October | 8.6 | 0.3 | 5.9 | 3 |
| 14-October | 8.7 | 0.3 | 9.6 | 0.8 |
| 29-October | 10.2 | 0.7 | 10.5 | 0.5 |
| 13-November | 12.1 | 0.7 | 11.5 | 0.4 |
| 25-November | 13.1 | 1.1 | 12.9 | 1.1 |

Table 4 below compares the fruit height, width, mass and rind color between fruit harvested from the parent 'Fallglo' as compared to the US Early Pride mandarin orange.

TABLE 4

Fruit Quality Fallglo scion vs Early Pride scion (Lake County, Florida)

| Scion | Height (mm) | Width (mm) | Mass (g) | Rind Color (a/b) |
|---|---|---|---|---|
| Fallglo | 64.8 | 79.0 | 225.2 | 0.197 |
| SD | ±3.7 | ±4.5 | ±35.2 | ±0.133 |
| Early Pride | 58.7 | 75.2 | 187.1 | 0.272 |
| SD | ±2.4 | ±3.1 | ±18.7 | ±0.112 |

TABLE 5

Comparison of 'US Early Pride' with 'Fallglo'.

| Trait | 'US Early Pride' | 'Fallglo' |
|---|---|---|
| Maturity | mid October | early October |
| Seeds/fruit | <1 | 20-40 |
| RHS rind color | RHS 22a | RHS 22a |
| Rind texture | smooth | smooth |
| Fruit weight | 145 g | 150 g |
| Fruit height/width | 0.86 | 0.88 |
| Alternate bearing | minimal | minimal |

Table 6 is another comparison of fruit quality comparing the Fallglo scion (parent plant) to the US Early Pride scion on three different dates of harvest.

TABLE 6

Fruit Quality Fallglo scion vs Early Pride scion (Lake County Florida)

| Date | Scion | Brix | BAR | Color Number |
|---|---|---|---|---|
| 31-October | Fallglo | 11.0 | 8.64 | 43.0 |
| | Early Pride | 10.7 | 9.57 | 42.2 |
| 21-November | Fallglo | 11.5 | 8.71 | 44.3 |
| | Early Pride | 11.6 | 10.56 | 43.7 |
| 4-December | Fallglo | 12.3 | 9.72 | 45.5 |
| | Early Pride | 11.8 | 11.63 | 44.8 |

Color number is a value that is determined by measuring juice color with a Greytag Macbeth Color Eye. The color number is derived from an equation (State of Florida, Department of Citrus Official rules affecting the Florida Citrus Industry, chapter 20-65 (20-65.005 Calculation)). Testing was done by offering consumers two cups containing segments of either Fallglo or US Early Pride. They did not know what they were testing, just asked to identify which sample they preferred.

Table 7 shows results of consumer testing with Fallglo and Early Pride. 53% of the respondents indicated that the absence of seeds was important.

TABLE 7

Consumer Test Results

| Group | Respondents | Preference | % |
|---|---|---|---|
| All | 255 | | |
| | 113 | Fallglo | 44.3 |
| | 142 | Early Pride | 55.7 |
| Males | 104 | | |
| | 47 | Fallglo | 45.2 |
| | 57 | Early Pride | 54.8 |
| Females | 145 | | |
| | 63 | Fallglo | 43.4 |
| | 82 | Early Pride | 56.6 |

Respondents is the number of folks who tasted fruit and provided a response, obviously, we kept track of sex of the respondents. The % column is the number of respondents that preferred one selection over the other, divided by the total number of respondents.

We claim:

1. A new and distinct variety of mandarin tree, substantially as illustrated and described herein, called 'U.S. Early Pride' characterized as being low seeded.

* * * * *